United States Patent [19]

Jautelat et al.

[11] 4,267,381
[45] May 12, 1981

[54] PREPARATION OF SIDE-CHAIN FLUORINATED 3,3-DIMETHYL-BUTAN-2-ONE

[75] Inventors: Manfred Jautelat, Burscheid; Jörg Stetter, Wuppertal; Dieter Arlt, Cologne; Wolfgang Krämer, Wuppertal, all of Fed. Rep. of Germany

[73] Assignee: Bayer Aktiengesellschaft, Leverkusen, Fed. Rep. of Germany

[21] Appl. No.: 77,447

[22] Filed: Sep. 20, 1979

[30] Foreign Application Priority Data

Oct. 6, 1978 [DE] Fed. Rep. of Germany ....... 2843767
May 10, 1979 [DE] Fed. Rep. of Germany ....... 2918895

[51] Int. Cl.³ .............................................. C07C 47/14
[52] U.S. Cl. ................... 568/419; 568/393; 568/394
[58] Field of Search ....................... 260/593 H, 601 H; 568/393, 419, 394

[56] References Cited

U.S. PATENT DOCUMENTS

| 2,606,209 | 8/1952 | Wilzbach | 260/593 H |
| 3,480,661 | 11/1969 | Rust et al. | 260/583 H |
| 3,976,469 | 8/1976 | Arnekley et al. | 260/593 H |

FOREIGN PATENT DOCUMENTS

| 710129 | 7/1941 | Fed. Rep. of Germany . |
| 2632602 | 1/1978 | Fed. Rep. of Germany . |

OTHER PUBLICATIONS

Houben-Weyl, vols. IX388-390 and 663-667.
Beilstein H. 1, E 111 3289, 3306.
Beilstein H. 1, E IV 4030, 4132.
J. Chem. Sco. (1932), p 2667-2673, (London) Morgan et al.
Bull. Sco. Chem. France (1964), 2849-2853.
J. Org. Chem. vol. 35, No. 7 (1970), 2391-2393, Lumma et al.
European Searc Report with Science Progress, vol. 58 (1970).

*Primary Examiner*—Werren B. Lone
*Attorney, Agent, or Firm*—Sprung, Felfe, Horn, Lynch & Kramer

[57] ABSTRACT

A fluorine derivative of 3,3-dimethyl-butan-2-one, of the formula

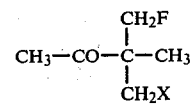

in which
X is hydrogen or fluorine, is produced by reacting a metal fluoride in a diluent and at elevated temperature with a sulphonic acid ester of the formula

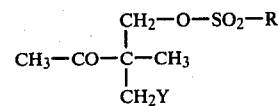

in which
R is optionally substituted alkyl or optionally substituted aryl, and
Y is hydrogen or O—SO₂—R.

The product is useful in the synthesis of fungicides.

3 Claims, No Drawings

PREPARATION OF SIDE-CHAIN FLUORINATED 3,3-DIMETHYL-BUTAN-2-ONE

The present invention relates to certain new fluorine derivatives of 3,3-dimethyl-butan-2-one, which can be used as intermediates for the synthesis of plant protection agents, and to a process for their preparation.

It has already been disclosed that certain halogen derivatives of 3,3-dimethyl-butan-2-one are interesting intermediates for the preparation of plant protection agents; examples which may be mentioned here are 3,3-dimethyl-4-chloro-butan-2-one and 3,3-dimethyl-4-bromo-butan-2-one, which can be processed to end products which have a fungicidal activity (see DE-OS German Published Specification No. 2,632,602 and U.S. Ser. No. 964,215, now pending) and which have an antimicrobial activity (see U.S. Ser. No. 914,769, now pending). The corresponding fluorine compounds have not been disclosed hitherto.

The present invention now provides, as new compounds, the fluorine derivatives of 3,3-dimethyl-butan-2-one, of the general formula

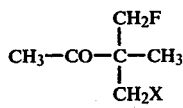

in which

X represents hydrogen or fluorine.

The invention also provides a process for the preparation of a fluorine derivative of 3,3-dimethyl-butan-2-one of the formula (I) in which a sulphonic acid ester of the general formula

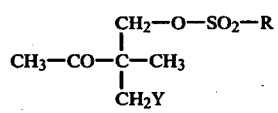

in which

R represents optionally substituted alkyl or optionally substituted aryl and

Y represents hydrogen or the group —O—SO$_2$—R, is reacted with a metal fluoride in the temperature range of about 80° to 250° C., in a diluent.

The compounds according to the present invention are interesting intermediate products for the preparation of plant protection active compounds having a fungicidal action.

The substances according to the invention are unambiguously defined by the general formula (I). The following compounds may be mentioned individually: 3,3-dimethyl-4-fluoro-butan-2-one and 3,3-bisfluoromethyl-butan-2-one.

If 2,2-dimethyl-3-oxo-1-butyl methanesulphonate and potassium fluoride are used as the starting materials, the course of the reaction can be represented by the following equation:

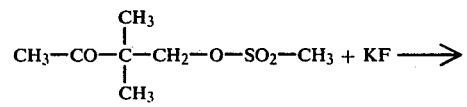

-continued

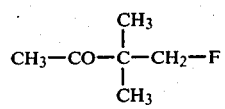

In the formula (II), R preferably represents alkyl with 1 to 4 carbon atoms, for example methyl, or aryl with 6 to 12 carbon atoms, for example phenyl or tolyl. Individual examples of the sulphonic acid esters of the formula (II) which may be mentioned are: 2,2-dimethyl-3-oxo-1-butyl methanesulphonate, 2,2-dimethyl-3-oxo-1-butyl ethanesulphonate, 2,2-dimethyl-3-oxo-1-butyl benzenesulphonate, 2,2-dimethyl-3-oxo-1-butyl p-toluenesulphonate, 2,2-dimethyl-3-oxo-1-butyl perfluorobutanesulphonate and 2-acetyl-2-methyl-propane-1,3-diol bis-methanesulphonate.

Sulphonic acid esters of the formula (II) used as starting materials are known (J.Org.Chem. 35, 2391 (1970)) and can be prepared by processes known from the literature, from the corresponding hydroxy-butanones and sulphonyl chlorides in the presence of bases (see, for example, Houben-Weyl, Methoden der Org. Chemie (Methods of Organic Chemistry), volume IX, pages 388 and 663, and also the data given in the preparative examples later in this text).

The metal fluorides used are, in general, alkali metal fluorides and alkaline earth metal fluorides, preferably sodium fluoride and potassium fluoride. These compounds are generally known.

Diluents which can be used are any of the polar organic solvents. These include, as preferences, sulpholane, dimethylformamide, dimethylsulphoxide, hexamethylphosphoric acid triamide, ethylene glycol, diethylene glycol, triethylene glycol, tetraethylene glycol and higher condensed polyethers.

The reaction temperatures can be varied within a relatively wide range. In general, the reaction is carried out at from 80° to 250° C. and preferably at about 100° to 200° C.

The compounds according to the invention can be prepared either under atmospheric pressure or under reduced pressure. According to a particular embodiment, the reaction is carried out under a pressure of about 10 to 100 mbars and the resulting reaction product is immediately distilled off from the reaction mixture.

When carrying out this process, the sulphonic acid ester and metal fluoride are, in general, employed in a molar ratio of 1:1 to 1:10, preferably 1:1.5 to 1:3.

As already mentioned, the fluorine derivatives of 3,3-dimethyl-butan-2-one of the formula (I) are interesting intermediate products. They can easily be converted into a halogenoketone of the general formula

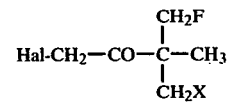

in which

X has the meaning stated above and

Hal represents chlorine or bromine, by adding chlorine or bromine to the compound of the formula (I) in an inert organic solvent at room temperature, or, for example, by reacting the compound of the formula (I) with a customary chlorinating agent, such as sulphuryl chloride, at 20° to 60° C. (see also the preparative examples given later).

A halogenoketone of the formula (III) can also be reacted with a phenol (a so-called "Williamson ether synthesis"; in this context see U.S. Ser. No. 964,215), a compound of the general formula $$Z_n \underset{}{\underbrace{\bigcirc}} -O-CH_2-CO-\underset{\underset{CH_2X}{|}}{\overset{\overset{CH_2F}{|}}{C}}-CH_3 \quad (IV),$$

in which
X has the meaning stated above,
Z represents halogen, alkyl, nitro, cyano, alkoxycarbonyl or optionally substituted phenyl and
n represents 0, 1 or 2,
being obtained. A compound of the formula (IV) can be converted by further halogenation, preferably with sulphuryl chloride or with bromine, into a fluorinated 1-chloro- or 1-bromo-1-phenoxy-3,3-dimethyl-butan-2-one, which can be reacted smoothly with an azole; for example, a compound of the general formula $$Z_n \underset{}{\underbrace{\bigcirc}} -O-\underset{\underset{Az}{|}}{CH}-CO-\underset{\underset{CH_2X}{|}}{\overset{\overset{CH_2F}{|}}{C}}-CH_3 \quad (V),$$

in which
X, Z and n have the meanings stated above and
Az represents 1,2,4-triazol-1-yl or 1,2,4-triazol-4-yl,
is obtained with 1,2,4-triazole.

The compounds of the formula (V) have powerful fungicidal properties and can therefore be used as plant protection agents.

The present invention is illustrated by the following preparative examples:

EXAMPLE 1

$$CH_3-CO-\underset{\underset{CH_3}{|}}{\overset{\overset{CH_3}{|}}{C}}-CH_2-O-SO_2-CH_3 \quad (a)$$

232 g (2 mol) of 3,3-dimethyl-4-hydroxy-2-butanone (for the preparation, see Beilstein H 1 E III 3239, IV 4030 and Bull. Soc. Chim. France 1964, 2849) were reacted in 700 ml of absolute pyridine at 0° to 5° C. with 229 g (2 mol) of methanesulphonyl chloride. After standing for 12 hours at 20° C., the reaction mixture was diluted with methylene chloride and extracted by shaking with ice-water. The organic phase was dried, freed from solvent in vacuo and fractionated through a column. At a boiling point of 106° to 120° C./0.12 mm Hg, 332 g (that is to say 86% of theory) of 2,2-dimethyl-3-oxo-butyl methanesulphonate were isolated.

$$(b) \quad CH_3-CO-\underset{\underset{CH_3}{|}}{\overset{\overset{CH_3}{|}}{C}}-CH_2F \quad (1)$$

38.8 g (0.2 mol) of 2,2-dimethyl-3-oxo-butyl methanesulphonate were added dropwise in the course of 2 hours, at 160° C. and 20 mbars, to a suspension of 23.2 g (0.4 mol) of dry potassium fluoride in 400 ml of distilled tetraethylene glycol, which was in a three-necked stirred flask with a descending condenser, and the mixture was stirred for a further 2 hours. The reaction product which was distilled out was condensed and collected in a descending condenser and in a downstream low-temperature trap. 20.9 g (0.177 mol, that is to say 89% of theory) of 3,3-dimethyl-4-fluoro-2-butanone, which under normal pressure boiled at 130° to 134° C., were thus obtained.

EXAMPLE 2

When the procedure according to Example 1 was followed but 17.4 g (0.3 mol) of potassium fluoride were reacted with 38.8 g (0.2 mol) of 2,2-dimethyl-3-oxobutyl methanesulphonate in 400 ml of distilled triethylene glycol at 120° C., the subsequent distillation gave 15.8 g (that is to say 67% theory) of 3,3-dimethyl-4-fluoro-2-butanone.

EXAMPLE 3

When the reaction according to Example 1 was carried out in 300 ml of hexamethylphosphoric acid triamide as the diluent, 3,3-dimethyl-4-fluoro-2-butanone was obtained in a yield of 53% of theory.

EXAMPLE 4

$$CH_3-CO-\underset{\underset{CH_2-O-SO_2-CH_3}{|}}{\overset{\overset{CH_2-O-SO_2-CH_3}{|}}{C}}-CH_3 \quad (a)$$

66 g (0.5 mol) of 3-oxo-2,2-bis-[hydroxymethyl]-butane (for the preparation, see Beilstein H 1, E III 3306, IV 4132 and J. Chem. Soc., London 1932, 2671) were dissolved in 300 ml of 1,2-dichloroethane, 114.5 g (1 mol) of methanesulphonyl chloride were added dropwise and 158 g (2 mol) of pyridine were added dropwise at 0° to 5° C. The reaction mixture was stirred for a further 15 hours at room temperature and the batch was then introduced into 600 ml of ice-water and 100 ml of concentrated hydrochloric acid. A solid precipitated out and this was filtered off. The aqueous phase was extracted with 1 liter of methylene chloride; the solid was dissolved in the methylene chloride phase, the organic phase was dried over sodium sulphate, the solvent was distilled off under a waterpump vacuum and the residue was suspended in 200 ml of ether. 100 g (about 70% of theory) of 2-acetyl-2-methyl-propane-1,3-diol bismethanesulphonate with a melting point of 105° to 108° C. were obtained.

$$(b) \quad CH_3-CO-\underset{\underset{CH_2F}{|}}{\overset{\overset{CH_2F}{|}}{C}}-CH_3 \quad (2)$$

400 ml of tetraethylene glycol and 46.4 g (0.8 mol) of potassium fluoride were initially introduced into a three-necked flask provided with a stirrer, a dropping funnel and a Liebig condenser with a cooled receiver and the mixture was heated to 170° C. A water-pump vacuum (pressure about 20 to 30 mbars) was applied to the adaptor of the Liebig condenser. 57.6 g (0.2 mol) of 2-acetyl-2-methyl-propane-1,3-diol bismethanesulphonate, dissolved in 100 ml of tetraethylene glycol, were then added dropwise in the course of 45 minutes. The 3,3-bisfluoromethyl-butan-2-one which formed was distilled off during the reaction into the cooled receiver. After the dropwise addition, distillation was continued for a further 1 hour at 175° C.

The distillate collected was then redistilled. 14 g (about 51.5% of theory) of 3,3-bisfluoromethyl-butan-2-one with a boiling point of 43° to 46° C./12 mm Hg were obtained.

The use of the novel compounds in further syntheses is shown in the following example:

EXAMPLE 5

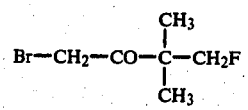 (a)

480 g of bromine were slowly added dropwise to a mixture of 354 g (3 mol) of 3,3-dimethyl-4-fluoro-2-butanone (see Example 1) and 2000 ml of ether at 20° to 30° C., while cooling and stirring. The yellowish solution was then stirred at 20° C. for a further 1 hour, and 500 ml of water were subsequently added carefully. The ether phase was separated off, washed several times with water and dried over sodium sulphate. After distilling off the solvent, the residue was distilled under a water-pump vacuum. 472 g (80% of theory) of 1-bromo-3,3-dimethyl-4-fluoro-2-butanone of boiling point 80° to 90° C./11 mm Hg were obtained.

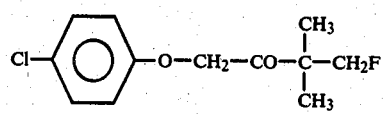 (b)

157 g (0.79 mol) of 1-bromo-3,3-dimethyl-4-fluoro-2-butanone were added dropwise to a stirred mixture of 102 g (0.79 mol) of p-chlorophenol and 110 g (0.79 mol) of powered potassium carbonate in 500 ml of acetone at 20° to 30° C., while cooling. The mixture was subsequently stirred at 20° C. for 2 hours, the inorganic salt was filtered off and the filtrate was concentrated. The residue was distilled under a high vacuum. 175 g (90% of theory) of 1-(4-chlorophenoxy)-3,3-dimethyl-4-fluoro-2-butanone of boiling point 112° to 119° C./0.05 mm Hg were obtained.

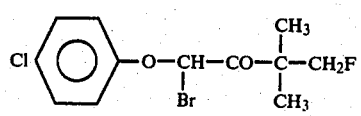 (c)

175 g (0.71 mol) of 1-(4-chlorophenoxy)-3,3-dimethyl-4-fluoro-2-butanone were dissolved in 500 ml of methylene chloride, and 114 g (0.71 mol) of bromine were added dropwise at 20° to 30° C., while stirring and cooling. The mixture was subsequently stirred at 20° C. for 2 hours, 200 ml of water were added carefully and the methylene chloride phase was washed several times with ice-water and dried over sodium sulphate. After distilling off the solvent in vacuo, the residue was recrystallized from cyclohexane. 180 g (78% of theory) of 1-bromo-1-(4-chlorophenoxy)-3,3-dimethyl-4-fluoro-2-butanone of melting point 73° to 75° C. were obtained.

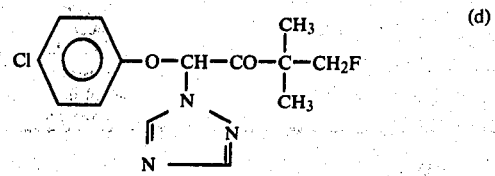 (d)

87 g (0.27 mol) of 1-bromo-1-(4-chlorophenoxy)-3,3-dimethyl-4-fluoro-2-butanone were dissolved in 200 ml of acetone and the solution was added dropwise to a boiling solution of 46 g (0.66 mol) of 1,2,4-triazole in 200 ml of acetone. After heating the mixture under reflux for one hour, the solvent was removed in vacuo, the residue was taken up in methylene chloride, the methylene chloride mixture was washed several times with water and the organic phase was dried over sodium sulphate. After removing the solvent in vacuo, the residue was crystallized with petroleumm ether. 75 g (89% of theory) of 1-(4-chlorophenoxy)-3,3-dimethyl-4-fluoro-1-(1,2,4-triazol-1-yl)-2-butanone of melting point 60° to 63° C. were obtained.

The following example shows, for example, the superior action of 1-(4-chlorophenoxy)-3,3-dimethyl-4-fluoro-1-(1,2,4-triazol-1-yl)-2-butanone in comparison with the analogous 4-chloro compound:

EXAMPLE 6

Powdery mildew of barley (*Erysiphe graminis* var. *hordei*) (fungal disease of cereal shoots)/systemic The active compound was used as a pulverulent seed treatment agent. This was prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3 × 12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had developed their first leaf, they were dusted with fresh spores of *Erysiphe graminis* var. *hordei* and grown on at 21–22 deg.C and 80–90% relative atmospheric humidity and 16 hours' exposure to light. The typical mildew pustules formed on the leaves over the course of 6 days.

The degree of infection was expressed as a percentage of the infection of the untreated control plants. Thus, 0% denoted no infection and 100% denoted the same degree of infection as in the case of the untreated control. The more active the compound, the lower was the degree of mildew infection.

The active compounds and concentrations of active compound in the seed treatment agent, as well as the amount used of the latter, and the percentage infection with mildew can be seen from the table which follows:

TABLE 1

| Active compounds | Active compound concentration in the dressing agent in % by weight | Amount of dressing agent used in g/kg of seed | Infection in % of the untreated control |
|---|---|---|---|
| 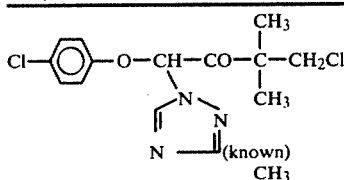 (known) | 10 | 2 | 100 |
| 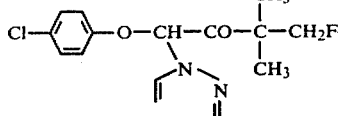 | 10 | 2 | 0.0 |

It will be appreciated that the instant specification and examples are set forth by way of illustration and not limitation, and that various modifications and changes may be made without departing from the spirit and scope of the present invention.

We claim:

1. A fluorine derivative of 3,3-dimethyl-butan-2-one, of the formula

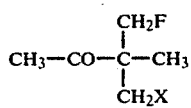

in which
X is hydrogen or fluorine.

2. A compound according to claim 1, wherein such compound is

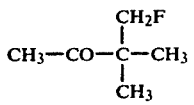

3. A compound according to claim 1, wherein such compound is

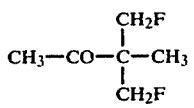

* * * * *